United States Patent [19]

Chu

[11] Patent Number: 4,776,890

[45] Date of Patent: Oct. 11, 1988

[54] PREPARATION OF COLLAGEN HYDROXYAPATITE MATRIX FOR BONE REPAIR

[75] Inventor: George Chu, Sunnyvale, Calif.

[73] Assignee: Collagen Corporation, Palo Alto, Calif.

[21] Appl. No.: 35,277

[22] Filed: Apr. 3, 1987

Related U.S. Application Data

[63] Continuation-in-part of Ser. No. 810,878, Dec. 18, 1985, abandoned.

[51] Int. Cl.$^4$ .................. C09K 3/00; C08L 89/00; A61C 8/00
[52] U.S. Cl. ............................... 106/161; 106/35; 433/201.1; 424/95
[58] Field of Search ................... 106/161, 35

[56] References Cited

U.S. PATENT DOCUMENTS

| | | | |
|---|---|---|---|
| 3,767,437 | 10/1973 | Cruz | 106/161 |
| 3,913,229 | 10/1975 | Driskell | 433/228.1 |
| 4,097,935 | 7/1978 | Jarcho | 106/35 |
| 4,186,486 | 2/1980 | Gordon | 403/201.1 |
| 4,349,470 | 9/1982 | Battista | 106/125 |
| 4,451,235 | 5/1984 | Okuda et al. | 106/35 |
| 4,488,911 | 12/1984 | Luck et al. | 106/161 |
| 4,516,276 | 5/1985 | Mittelmeir | 128/92 C |
| 4,557,764 | 12/1985 | Chu | 260/123.7 |
| 4,563,350 | 6/1986 | Nathan et al. | 106/161 |

*Primary Examiner*—Theodore Morris
*Attorney, Agent, or Firm*—Ciotti, Murashige, Irell & Manella

[57] ABSTRACT

An improved process for obtaining a matrix of mineral particles in reconstituted atelopeptide collagen comprises reconstituting a mixture of mineral particles with collagen in solution. This process results in a matrix of collagen containing the mineral particles which, when wetted, is malleable and retains its integrity.

10 Claims, No Drawings

PREPARATION OF COLLAGEN HYDROXYAPATITE MATRIX FOR BONE REPAIR

This application is a continuation-in-part of application Ser. No. 810,878, filed Dec. 18, 1985 abandoned.

TECHNICAL FIELD

The invention relates to the field of hard tissue repair, and to the preparation of suitable materials to effect it. Specifically, it relates to a method for preparing a mineral-embedded collagen matrix containing the mineral component coated with collagen, which is malleable and suitable for bone augmentation.

BACKGROUND OF THE INVENTION

It has been known for decades that the chief structural materials in bone tissue are collagen and a mineral, hydroxylapatite. It is therefore, perhaps, not surprising that attempts to manufacture materials suitable for bone replacement have employed one or the other or both of these materials in some form. Various forms of collagen have been used to construct bone repair matrices (see, for example, U.S. Ser. No. 752,447, filed July 5, 1985, assigned to the same assignee). It has also been attempted to use the mineral component by itself, either as hydroxylapatite or a closely related form of calcium phosphate. See, for example, U.S. Pat. No. 3,913,229 and U.S. Pat. No. 4,097,935.

There is also literature on the use of mixtures of ceramic and collagen materials in bone repair or in dental reconstruction. At least two reports indicated that such mixtures were not effective in mediating effective bone replacement (Lemmons, J., et al, Second World Congress on Biomaterials, Washington, D.C., April 27–May 1, 1984, p. 6; Levy, P., et al, *J Periodontol* (1981): 303–306). Such materials were also used to construct dental prostheses as disclosed in U.S. Pat. No. 4,186,486. In these three previously cited references, the nature of the collagen used was unspecified, and it is not possible to discern the process for making the implant material or dental prostheses.

Others have used preformed collagen fibers or insoluble collagen in some form to mix with the mineral component. Batista, U.S. Pat. No. 3,443,261, prepares the mixture by using a water insoluble microcrystalline partial salt of collagen and calcium phosphate; Cruz, U.S. Pat. No. 3,767,437, also utilizes the precipitated calcium salt of collagen in the reported compositions. Gross, B. D., et al, *Oral Surg* (1980) 49: 21–26, used reconstituted collagen fibers in admixture with hydroxylapatite crystals. U.S. Ser. No. 717,072, filed Mar. 28, 1985, assigned to the same assignee and incorporated herein by reference, discloses methods of preparing ceramic/collagen mixtures using atelopeptide reconstituted fibrillar collagen. In addition, U.S. Pat. No. 4,516,276 to Mittelmeier employs collagen as a fleece described as a grid or network which is then dusted with apatite powder or granules, or the fiber material is mixed with mineral before being formed into layers for implantation into bone.

Others have employed collagen in solution as the organic component in forming the mixture. Perhaps the most literal approach has been that of Miyata et al, U.S. Pat. No. 4,314,380, wherein artifical bone is prepared using, as the inorganic component, animal bone which has been treated to remove the organics and then immersed in an atelopeptide collagen solution. Batista, U.S. Pat. No. 4,349,470, describes the preparation of bone prostheses by mixing a calcium phosphate mineral, which is described to include hydroxylapatite and a variety of other forms, with a protein solution in dilute hydrogen peroxide with the addition of cross-linking agents. This is described to result in a hydrogel calcium phosphate composition which can then be dried to include small uniformly dispersed bubbles. Japanese patent application No. J58/058041, published Oct. 5, 1981, describes the use of a porous calcium phosphate mineral block which is then dipped in collagen solution to coat the pores.

Other patents which relate to collagen-based bone repair preparations include the following. U.S. Pat. No. 4,488,911 to Luck et al. discloses a method of preparing dispersed fibrillar collagen which uses shear forces to order fibrils during aggregation; the method is used to prepare collagen membranes on a surface. U.S. Pat. No. 4,563,350 to Nathan discloses an admixture of a protein osteoinductive factor derived from bone with a solution containing non-fibrillar collagen. U.S. Pat. No. 4,440,750 to Glowacki et al. shows a mixture or dispersion of bone powder and fibrous collagen in aqueous solution.

It is apparent from the number and nature of the disclosures available in the art that the method of preparing the collagen, mineral, or mixed materials is of utmost importance in determining the characteristics of the product. The resulting material may or may not be effective, depending on the way in which the collagen and mineral components are handled individually and together. The present invention offers a novel preparation for collagen/mineral mixtures which results in a material of superior properties for repair of bone defects, and in particular for procedures which involve augmentation of bone structures.

The present invention also provides a collagen/mineral matrix which displays physical strength far superior to that achieved by prior art admixtures of collagen and mineral. This is evidenced, as will be described, by a product having a much higher compressive modulus than known collagen/mineral compositions.

DISCLOSURE OF THE INVENTION

The invention provides a bone repair material which is malleable when moistened and retains its integrity for shaping and use an an augmentation material for hard tissue. The material is an array of mineral particles which are embedded in a collagen matrix, wherein the particles are surrounded by a collagen coat and retained in a collagen matrix without cross-linking of the collagen. This matrix results from a preparation procedure using the collagen in soluble form for mixing with mineral particles and treating with a solution of a precipitating buffer to precipitate the collagen around the particles. The product, when dried, becomes a useful matrix which, when remoistened, is both malleable and retains its structural integrity.

Thus, in one aspect, the invention relates to a method for preparing a collagen/mineral matrix, which method comprises mixing mineral particles with collagen in solution, treating the resulting suspension against a neutralizing buffer, and drying the resultant. The invention also relates to the product of this process and to methods of hard tissue repair using this material.

MODES OF CARRYING OUT THE INVENTION

The heart of the invention is the formation of a uniform matrix of collagen around mineral particles by treating these particles with collagen in solution and reconstituting the collagen around the particles by treating with a precipitating buffer. The reconstitution is preferably carried out by dialyzing the mineral suspension in collagen solution against the precipitating buffer, thus assuring a uniform distribution around the particles. It is also preferred that the dialysis be carried out under conditions wherein the dialysis container maintains sterile conditions for formation of the desired matrix such that further sterilization is unnecessary.

The nature of the mineral particles is in keeping with the projected utility of the resulting matrix. While it is possible to use a porous block of mineral, it is preferred to utilize a suspension wherein the particles are of a dimension determined by the projected use of the matrix. For example, for dental uses, which require, in general, more flexibility, smaller particles are used, preferably 40/60 mesh, which corresponds to a particle dimension of 215–420 microns. However, for supplementation of bone structures, especially those which bear some stress, larger particles are preferred, for example 20/40 mesh, which represents diameters of 420–840 microns. The mineral itself is, in general, a form of calcium phosphate, preferably hydroxylapatite, which is believed to be most closely related to the mineral content of bone. However, other forms of calcium phosphate, such as tricalcium phosphate, dicalcium phosphate, carbonate apatite, chloroapatite, fluoroapatite, and mixtures of the foregoing, could also be used. Hydroxylapatite is preferred. The hydroxylapatite particles are supplied in dried form, but may also be suspended in aqueous medium wherein the aqueous medium is compatible with the collagen in solution. The nature of the hydroxylapatite or other mineral particles is significant, as it determines the characteristics of the matrix, but does not itself form part of the invention. Any suitable mineral particles, commercially obtained or otherwise, of proper dimension for the intended use, may be used.

The collagen in solution can also be from a variety of sources but is a purified atelopeptide form to reduce immunogenicity. The collagen can be prepared from a variety of mammalian sources, most conveniently bovine or porcine skins, and is treated with suitable proteolytic enzymes to remove the telopeptides. The preparation of such a solubilized collagen is well known in the art, and, indeed, commercial preparations of collagen in solution (CIS) are available, such as Zygen® CIS, available from Collagen Corporation, Palo Alto, Calif. These commercial preparations, however, may need to be concentrated before using them for making the matrix by reconstitution and resolubilization. The collagen solution which is useful in the method of the invention typically has a collagen concentration of 35 mg/ml–120 mg/ml, preferably around 65 mg/ml. Zygen® has a concentration of 3 mg/ml.

While the preparation of purified soluble collagens is known in the art, for convenience, a brief resume of a suitable procedure follows: Typically animal skin is softened by soaking it in mild acid and then removing extraneous materials such as hair, epidermis, and fat. The skin is then soaked again in mild acid and comminuted by grinding, mincing, or the like before solubilizing under nondenaturing conditions by digesting with a proteolytic enzyme other than a collagenase. The digestion is preferably done at low pH and at low temperature, the pH normally being in the range of 1.5–5 and the temperature 5° C.–25° C. For example, the comminuted tissue may be dispersed in a dilute HCl solution of pH about 2 at 20° C. and then treated with a suitable enzyme at a concentration of 0.1–10% by weight, based on the collagen. Suitable enzymes include pepsin, papain, and trypsin, preferably trypsin, and the incubation period for the digestion lasts from two days to about two weeks. The solubilization may be monitored by determining the viscosity of the solution, which should stabilize at a constant level.

After this incubation, the enzyme is deactivated and the solution treated to remove impurities. Such procedures may include precipitation of the denatured enzymes and filtration or centrifugation to remove the precipitate and cell debris, and dialysis to remove soluble small molecules. Procedures for removing solid impurities by sedimentation or filtration are well known. The resulting supernatant is optionally further purified by using ion-exchange chromatography or dialysis and the purified material further concentrated to produce a substantially pure atelopeptide collagen solution. The collagen is maintained in solution by keeping the pH at a low value, preferably below 3–4. The pH, of course, determines the permissible concentration level for the CIS.

Rather than starting from scratch, the collagen in solution for use in the invention may also be prepared by using commercial reconstituted collagen preparations such as Zyderm® collagen implant. This commercial preparation is an atelopeptide form of collagen and can be used directly by solubilizing the material using dilute mineral or carboxylic acids such as HCl or acetic acid. The concentration of acid is maintained at a level so as to solubilize the collagen in the appropriate concentration range. The solubilization may be accomplished either directly or by dialyzing the preparation against the acid solution.

In the process of the invention, the two components of the matrix, collagen in solution and the mineral particles, are mixed in a suitable ratio between about 50% mineral/50% CIS to about 80% mineral/20% CIS, the ratio here being given by weight and assuming a collagen concentration of 65 mg/ml. The desired ratio clearly depends on the use for which the resulting matrix is intended, the nature of the mineral particles and the desired properties of the resultant. The range of ratios is, of course, not entirely discrete, and a continuum of workable relative amounts is characteristic of the nature of the process. In any event, because the concentration of collagen in solution form is never greater than about 0.12 g/ml—i.e., approximately 12% by weight, assuming a density of 1 g/ml for the solution, the percentage of collagen in the final product, calculated on a weight basis of collagen to total solids, is never more than 10%, and may be as little as 0.5%. However, such low concentrations of collagen are not preferred. Preferable ranges on a weight basis for collagen range from about 1% to 10%.

After mixing the mineral particles with the collagen in solution, the mixture is treated with a precipitating buffer solution. In general, this buffer solution can be any neutralizing material adjusted to a suitable pH which will raise the pH of the solution to around neutrality. In a preferred approach, rather than direct neutralization with a buffer of higher pH, the mixture is dialyzed against an excess of buffer maintained at the desired neutral pH value and adjusted to ionic strength conditions compatible with physiological environments. This approach further offers the capability of using a sterile solution of collagen (for example, this can be sterilized by filtration) along with an aseptic form of the mineral and maintaining these sterile conditions by using a dialysis bag with a 50,000 dalton molecular weight cut-off capability, which constitutes a primary sterile barrier. This permits the dialyzate to be maintained under sterile conditions without the necessity of artificial processes which may disrupt the matrix by causing degradation or cross-linking.

Preferred buffer solutions for dialysis include phosphate buffers maintained at physiological pH—i.e., about 7.4—and supplemented with salt to maintain a physiological ionic strength. A suitable mixture is 0.02M sodium phosphate, 0.13M NaCl at pH 7.4.

The mixture is then treated with the neutralizing solution, preferably by dialyzing at low temperature, and then incubated for 12–36 hours, preferably around 24 hours, at approximately 37° C. Lower incubation temperatures may also be used along with longer incubation times. After the fibers are reconstituted, the product is dried at 37° C. to obtain a sterile packaged material.

The collagen/mineral matrix so provided displays superior physical properties as evidenced by compressive modulus studies (see Example III). The matrix produced herein typically has a compressive modulus on the order of at least about 10–11N/cm$^2$. This is in contrast to the collagen/mineral admixtures of the prior art, which normally have compressive moduli on the order only 1–5N/cm$^2$. The substantially improved physical strength of the present invention renders the material far more resistant to deformation than prior art admixtures.

For use, the dried material is moistened by soaking for 10–15 min in sterile water to obtain the desired malleability. The material maintains its integrity during this moistening process and becomes capable of shaping into suitable filler materials for bone repair. Particularly suitable indications for use of this material are alveolar ridge augmentation, implants for chin or cheekbones, and periodontal use. In general, the techniques for implanting the material are those known and used in the art, but the general approach is first to shape the filler into the desired configuration and then to permit it to equilibrate with the body fluids to assume its position in the defect or provide the needed augmentation.

The material of the invention may optionally be cross-linked by treating with suitable cross-linking agents, but this is, in fact, undesirable, because bone ingrowth may be discouraged by tightening the matrix further. Also, heat treatment appears undesirable, as this may cause cross-linking. Accordingly, the dialysis procedure in which the container for dialysis then serves as a container for the resulting matrix, is advantageous, as further exposure to the environment is avoided and sterility is maintained.

EXAMPLES

The following illustration is intended to demonstrate an appropriate protocol for carrying out the invention. However, it is not to be construed as limiting, and variations on this protocol, as defined by the claims, are permitted.

PREPARATION A

Preparation of Concentrated Collagen in Solution

A 90 ml sample of Zygen ® CIS (3 mg/ml) was mixed with 10 ml 0.2M Na$_2$HPO$_4$, pH 11.2, at room temperature, and the precipitate collected by centrifugation. The precipitate was loaded into dialysis bags and dialyzed against 0.5M acetic acid until the precipitate was completely dissolved. The dialysis solution was then changed to 0.001M acetic acid and dialysis continued to equilibrium to maintain the collagen in solution form. The collagen concentration of the solution in the dialysis bag was determined by Biuret assay and adjusted to 65 mg/ml by addition of further amounts of 0.001M acetic acid.

Alternatively, rather than precipitation of the Zygen ® CIS, Zyderm ® collagen implant may be placed into the dialysis bags and dialyzed against acid as above to prepare the concentrated collagen in solution.

EXAMPLE I

Preparation of the Matrix

Thirty-five g of CIS prepared as in Preparation A at 65 mg/ml were mixed with 65 g of hydroxylapatite particles, 20/40 mesh, obtained from Orthomatrix, Dublin, CA. On a solids basis, this represents approximately 3.3% collagen. The mixture, which has a volume of approximately 50 ml, was loaded into a dialysis container having a molecular weight cut-off of 50 kd; the dialysis container was previously sterilized, and the collagen in solution previously sterilized by filtration. The materials were dialyzed against a solution containing 0.02M Na$_2$HPO$_4$, 0.13M NaCl, at pH 7.4, at 4° C. to equilibrium. After dialysis, the dialyzed mixture was transferred to a sterilized closed container and incubated at 37° C. for 24 hours. The mixture was then dried by evaporation at 37° C. to obtain the final product. This is a sterile hydroxylapatite in a dense fibrillar collagen matrix backing.

EXAMPLE II

Use in Bone Repair

The matrix prepared in Example I was soaked for 10 min in sterile distilled water. The resulting malleable material was then shaped under sterile conditions to form a suitable implant for augmentation of alveolar or facial structures.

EXAMPLE III

Compressive Modulus Studies

Hydroxylapatite/collagen composites were prepared by mixing and compressing hydroxylapatite with Zyderm ® Collagen Implant (Collagen Corporation) having a concentration of 65 mg/ml. Several samples were heat-treated at 60° C. for various periods of time as set forth in Table 1. A hydroxylapatite/collagen matrix was then prepared as described in Example I. Compression tests were carried out on the hydrated form of all samples to compare the compressive strength of all samples.

| Sample | Heat treatment time (hrs) | Compressive modulus, E (N/Cm$^2$) |
|---|---|---|
| HA/Collagen Mixture | Control | 1.25 |
| HA/Collagen Mixture, | 72 | 3.50 |

| Sample | Heat treatment time (hrs) | Compressive modulus, E (N/Cm$^2$) |
| --- | --- | --- |
| Heat treated at 60° | | |
| HA/Collagen Mixture, | 96 | 3.87 |
| Heat treated at 60° | | |
| HA/Collagen Mixture, | 120 | 4.0 |
| Heat treated at 60° | | |
| HA/Collagen Mixture, | 144 | 4.17 |
| Heat treated at 60° | | |
| HA/Collagen Mixture, | 168 | 4.54 |
| Heat treated at 60° | | |
| HA/Collagen Matrix | | 11.62 |

The compressive modulus (E) for each sample measured from stress-strain calculations indicated a much higher compressive modulus for the inventive matrix than for the hydroxylapatite/collagen admixtures. As may be seen in Table 1, the compressive modulus for the matrix (11.62N/cm$^2$) was almost ten times higher than that obtained for the simple admixture of hydroxylapatite with collagen (1.25N/cm$^2$).

I claim:

1. A method to prepare a mineral collagen matrix having mineral particles retained within a native collagen matrix, which method comprises dialyzing a mixture of mineral particles and non-fibrillar collagen in acidic solution against a reconstituting medium, said reconstituting medium comprising a precipitating, buffer solution selected so as to promote native collagen fiber formation.

2. The method of claim 1 wherein the mixture contains 1-10% collagen wt/wt of total solids.

3. The method of claim 1 wherein the reconstituting solution is phosphate buffer at physiological pH and ionic strength.

4. The method of claim 1 wherein the dialysis is conducted to maintain sterile conditions within the dialysis container.

5. The process of claim 4 which further includes drying the reconstituted matrix.

6. The process of claim 1 wherein the collagen in solution is at a concentration of 35-120 mg/ml.

7. The process of claim 1 wherein the mineral particles are hydroxylapatite particles.

8. The process of claim 7 wherein the hydroxylapatite is 20/40 or 40/60 mesh.

9. The matrix prepared by the method of claim 1.

10. A method for repairing bone defects which comprises administering to said defect the composition of claim 9.

* * * * *